United States Patent
Chen et al.

(10) Patent No.: US 8,460,801 B2
(45) Date of Patent: Jun. 11, 2013

(54) QUINOXALINE DERIVATIVES AND THEIR USE IN ORGANIC LIGHT-EMITTING DIODE DEVICE

(75) Inventors: Min Sheng Chen, Ta-sheh (TW); Yue Lin Du, Ta-Sheh (TW); Hsiao-Chan Liu, Ta-sheh (TW)

(73) Assignee: China Petrochemical Development Corp, Taipei (TW)

( * ) Notice: Subject to any disclaimer, the term of this patent is extended or adjusted under 35 U.S.C. 154(b) by 319 days.

(21) Appl. No.: 12/795,978

(22) Filed: Jun. 8, 2010

(65) Prior Publication Data

US 2011/0147720 A1    Jun. 23, 2011

(30) Foreign Application Priority Data

Dec. 18, 2009 (TW) .............................. 98143557 A

(51) Int. Cl.
*H01L 51/54* (2006.01)
*C07D 241/36* (2006.01)

(52) U.S. Cl.
USPC ........... 428/690; 257/40; 544/343; 548/305.1

(58) Field of Classification Search
None
See application file for complete search history.

(56) References Cited

U.S. PATENT DOCUMENTS

| 7,265,378 B2 | 9/2007 | Lecloux et al. |
| 2008/0091012 A1* | 4/2008 | Egawa et al. .................. 544/230 |
| 2009/0039774 A1* | 2/2009 | Horiba et al. .................. 313/504 |

FOREIGN PATENT DOCUMENTS

| EP | 2 065 378 A1 | 6/2009 |
| JP | 2009170814 A * | 7/2009 |

OTHER PUBLICATIONS

Machine English translation of JP 2009-170814 A. Jun. 8, 2012.*
Machine English translation of JP 2009-170814 A. Nov. 25, 2012.*
Jandke, M. et. al., Phenylquinoxaline Polymers and Low Molar Mass Glasses as Electron-Transport Materials in Organic Light Emitting Diodes, Macromolecules, 1998, vol. 31 (19) pp. 6434-6443.
Schmitz, et al., Efficient Screening of Electron Transport Material in Multi-Layer Organic Light Emitting Diodes by Combinatorial Methods, Phys. Chem. Chem. Phys.,1999, vol. 1, pp. 1777-1781.

* cited by examiner

*Primary Examiner* — Jennifer Chriss
*Assistant Examiner* — J. L. Yang
(74) *Attorney, Agent, or Firm* — Woodard, Emhardt, Moriarty, McNett & Henry LLP

(57) ABSTRACT

The present invention relates to novel quinoxaline derivatives and their use in an organic light-emitting diode device. The quinoxaline derivative is of luminescence and rigidity, can increase glass transition temperature (Tg) and has better thermal stability, and thus can be used as a hole transporting layer, a host or guest of an emitting layer or an electron transporting layer of an organic light-emitting diode device.

7 Claims, 1 Drawing Sheet

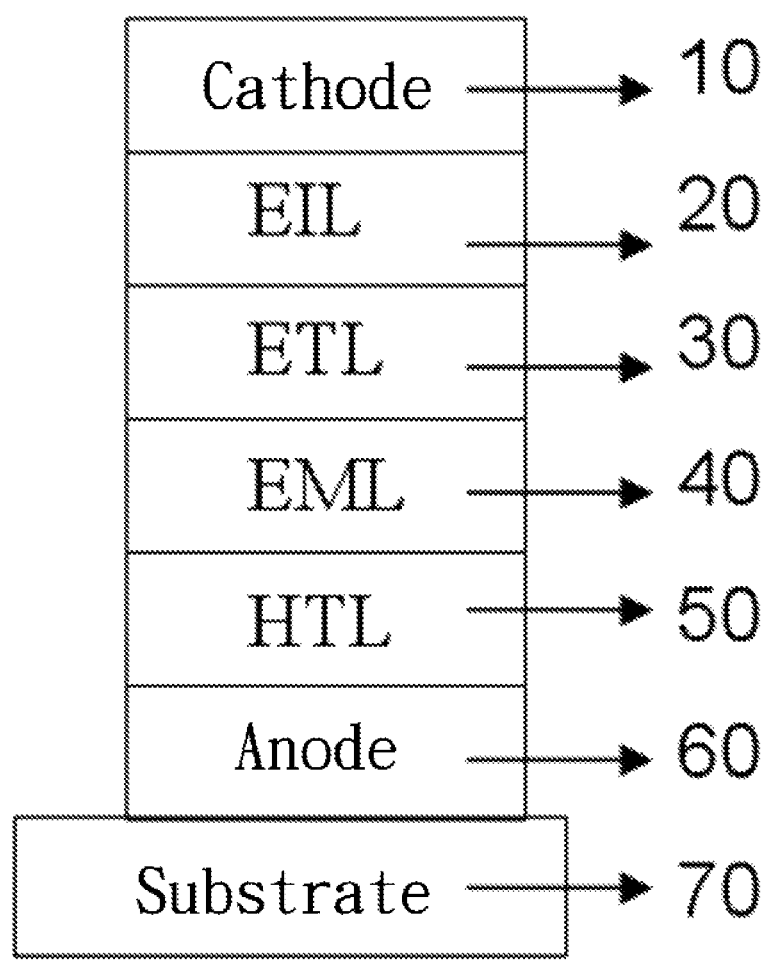

QUINOXALINE DERIVATIVES AND THEIR USE IN ORGANIC LIGHT-EMITTING DIODE DEVICE

FIELD OF THE INVENTION

The present invention relates to novel quinoxaline derivatives and their use in an organic light-emitting diode (OLED) device. In particular, the present invention relates to novel quinoxaline derivatives that can be used as a hole transporting layer, a host or guest of an emitting layer or an electron transporting layer of an organic light-emitting diode device.

BACKGROUND TO THE INVENTION

The electroluminescent phenomenon of organic materials was discovered by Pope et al. in 1963, when a 5 mm single layer anthracene crystal obtained by thermal evaporation was used as an emitting layer and the driving voltage for the organic light-emitting device thus produced must be as high as 100 V or above. In 1987, Dr. Ching W. Tang et al. of Eastman Kodak Company, USA, made a double layer device with an organic fluorescent dye by vacuum thermal evaporation, of which the driving voltage was smaller than 10 V. Currently, an OLED device is produced by lamination, in which an anode layer formed of a transparent conductive material such as indium tin oxide (ITO) is provided on a glass substrate, and on the anode layer, a hole transporting layer (HTL), an emitting layer (EML), a hole blocking layer (HBL), an electron transporting layer (ETL), an electron injection layer (EIL) and a cathode layer are provided in order.

The anode layer can be constituted of ITO, and the cathode layer can be constituted of metals having a low work function (such as Al, Mg or their alloys with other metals). The host or guest of the emitting layer can be constituted of metal complexes or common organic compounds. The hole blocking layer commonly uses organic compounds such as BCP (2,9-dimethyl-4,7-diphenyl-1,10-phenanthroline). The material for the hole transporting layer was mainly triarylamines, such as TPD (N,N'-diphenyl-N,N'-bis(3-methylphenyl)-1,1'-biphenyl-4,4'-diamine), NPB (N,N'-diphenyl-N,N'-bis(1-napthyl)-(1,1'-biphenyl)-4,4'-diamine), etc., in the past. The material for the electron transporting layer commonly uses Alq3 (Tris(8-hydroxyquinolinato) aluminum). The material for the host of an emitting layer commonly uses CBP (4,4'-bis(carbazol-9-yl)biphenyl). The material for the guest of a red light emitting layer commonly uses rubrene ((5,6,11,12)-Tetra-phenylnaphthacene), and the material for the guest of a green light emitting layer commonly uses Ir(ppy)$_3$ (Tris(2-phenylpyridine)iridium).

The organic light-emitting diode device is essentially composed of organic molecules, in which derivatives from quinoxaline that use it as their main structures have been used as the medium of organic electroluminescence. For example, the OLED device disclosed by Peter Strohriegl et al. uses a quinoxaline derivative as the material for the electron transporting layer (Macromolecules 1998, 31, 6434-6443), and the structure of its substituent includes Bis(phenylquinoxalines); the OLED device disclosed by Hans-Werner Schmidt et al. uses a quinoxaline derivative as the material for the electron transporting layer (Phys. Chem. chem. phys 1999, 1, 1777-1781), and the structure of its substituent includes spiroquinoxaline. The OLED device disclosed by EP 2065378 uses a quinoxaline derivative as the material for the electron transporting layer, and the structure of its substituent includes pyridyl, alkyl, aryl or arylene but does not include amino. The OLED device disclosed by U.S. Pat. No. 7,265,378 uses a quinoxaline derivative as the material for the electron transporting layer, and the structure of its substituent includes halogen, haloalkyl, aryl, etc., but does not include amino.

In the aforementioned OLED devices, those quinoxaline derivatives are mostly used as the material for the electron transporting layer, and it has not been disclosed that quinoxaline derivatives can be used as the materials for the hole transporting layer and the host or guest of the emitting layer simultaneously or solely. Generally speaking, the hole transporting layer, the electron transporting layer and the emitting layer are constituted of different main structural materials.

SUMMARY OF THE INVENTION

The object of the present invention is to provide novel organic materials of quinoxaline derivatives and to apply them to an organic light-emitting diode device. The quinoxaline derivative is of luminescence and rigidity, can increase glass transition temperature (Tg) and has better thermal stability, and thus can be used as a hole transporting layer, a host or guest of an emitting layer or an electron transporting layer of an organic light-emitting diode device.

FIG. 1 is a schematic diagram showing the structure of an organic light-emitting diode. As shown in FIG. 1, the organic electroluminescence device mainly comprises an anode 60, an organic emitting layer 40 and a cathode 10. The anode 60 is constituted by coating a glass substrate 70 with a transparent conductive ITO layer. The cathode 10 is a metal layer composed of, for example, aluminum (Al). A hole transporting layer (HTL) 50 is provided between the organic emitting layer 40 and the anode 60. An electron transporting layer (ETL) 30 and an electron injection layer (EIL) 20 are provided between the organic emitting layer 40 and the cathode 10.

In the aforementioned OLED device, a quinoxaline derivative of the present invention is used as the material for at least one of a host or guest of the emitting layer, the hole transporting layer and the electron transporting layer.

The quinoxaline derivative according to the present invention has a structure represented by formula (1):

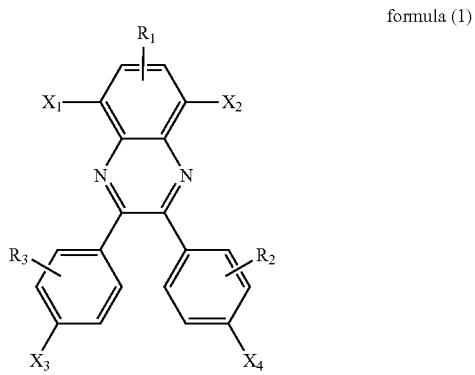

formula (1)

wherein $R_1$-$R_3$ are independently selected from the group consisting of hydrogen atom, amino group, $C_1$-$C_{20}$ fluorinated alkyl group, $C_3$-$C_{20}$ cycloalkyl group, $C_3$-$C_{20}$ fluorinated cycloalkyl group, $C_6$-$C_{20}$ aryl group, $C_6$-$C_{20}$ fluorinated aryl group, $C_4$-$C_{20}$ heterocyclic aryl group, $C_4$-$C_{20}$ fluorinated heterocyclic aryl group, $C_7$-$C_{20}$ alkylaryl group and $C_7$-$C_{20}$ fluorinated alkylaryl group, and $X_1$-$X_4$ are selected from the group consisting of the structures represented by the formulae (2)-(5):

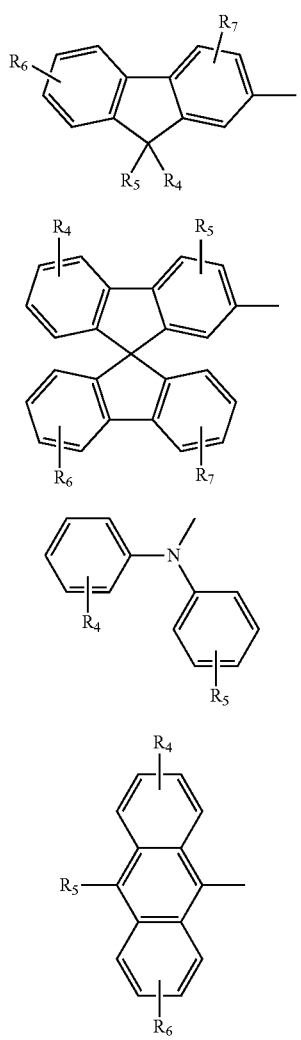

formula (2)

formula (3)

formula (4)

formula (5)

wherein $R_4$-$R_7$ are independently selected from the group consisting of hydrogen atom, amino group, $C_1$-$C_{20}$ fluorinated alkyl group, $C_3$-$C_{20}$ cycloalkyl group, $C_3$-$C_{20}$ fluorinated cycloalkyl group, $C_6$-$C_{20}$ aryl group, $C_6$-$C_{20}$ fluorinated aryl group, $C_4$-$C_{20}$ heterocyclic aryl group, $C_4$-$C_{20}$ fluorinated heterocyclic aryl group, $C_7$-$C_{20}$ alkylaryl group and $C_7$-$C_{20}$ fluorinated alkylaryl group.

The features and effects of the present invention are described in detail by the following embodiments, and also as set forth in applicants' Taiwanese priority application No. 098143557, filed Dec. 18, 2009, the entire contents of which are hereby incorporated herein by reference. However, those embodiments are used mainly to assist in understanding the present invention, but not to restrict the scope of the present invention.

DESCRIPTION OF PREFERRED EMBODIMENTS

First, a series of quinoxaline derivatives having the following structures are synthesized in accordance with the synthesis method that will be described later in the specification, and then applied to the test of OLED devices.

The quinoxaline derivative has the following structure when $X_3$ and $X_4$ are hydrogen atoms and $X_1$ and $X_2$ are 9,9'-dimethylfluorenyl groups:

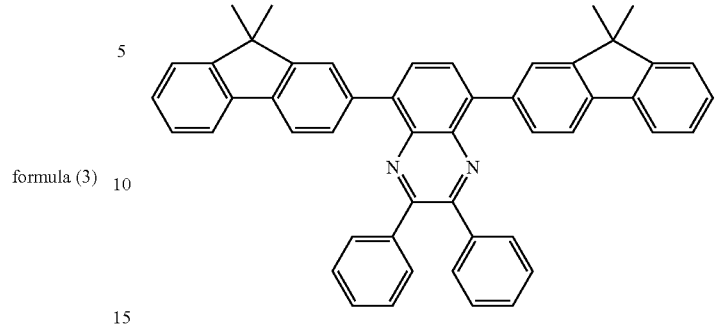

(Compound 1)

The quinoxaline derivative has the following structure when $X_3$ and $X_4$ are hydrogen atoms and $X_1$ and $X_2$ are 9,9'-spirobifluorenyl groups:

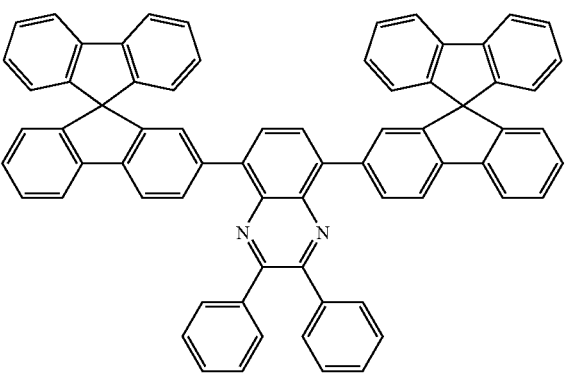

(Compound 2)

The quinoxaline derivative has the following structure when $X_1$ and $X_2$ are hydrogen atoms and $X_3$ and $X_4$ are 9,9'-spirobifluorenyl groups:

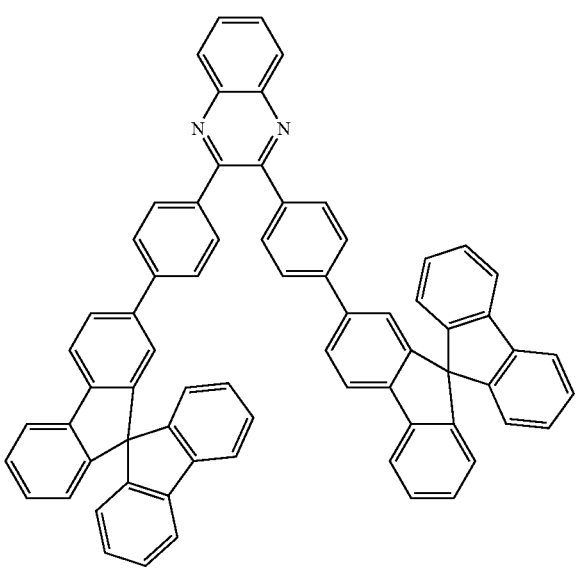

(Compound 3)

The quinoxaline derivative has the following structure when $X_3$ and $X_4$ are hydrogen atoms and $X_1$ and $X_2$ are anthryl groups:

(Compound 4)

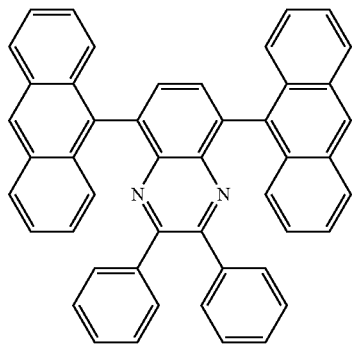

The quinoxaline derivative has the following structure when $X_3$ and $X_4$ are 9,9'-spirobifluorenyl groups and $X_1$ and $X_2$ are diphenylamino groups:

(Compound 5)

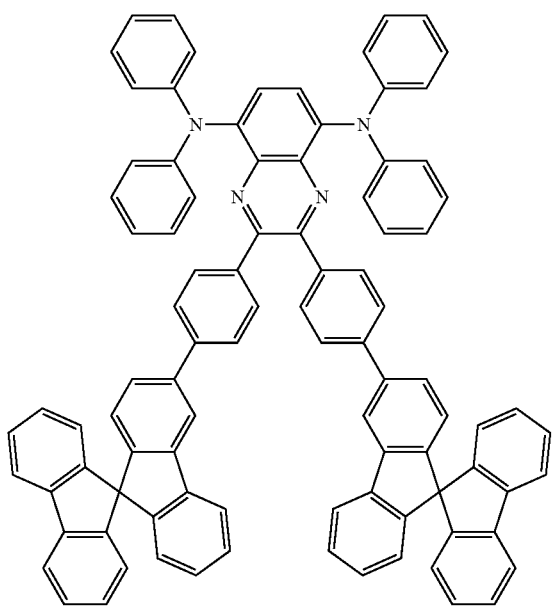

The quinoxaline derivative has the following structure when $X_3$ and $X_4$ are diphenylamino groups and $X_1$ and $X_2$ are 9,9'-dimethylfluorenyl groups:

(Compound 6)

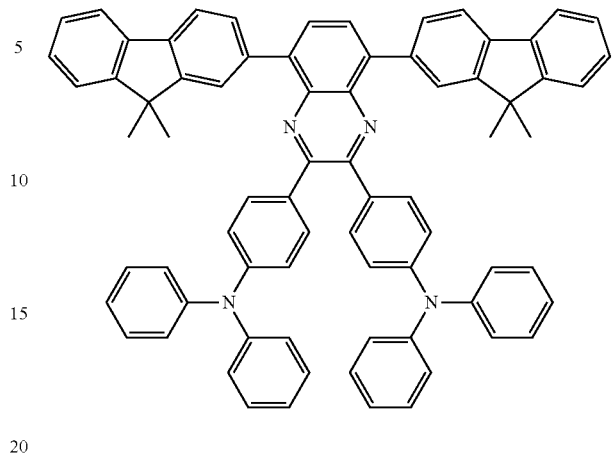

The synthesis method for the quinoxaline derivatives according to the present invention is described below.

(The Synthesis of Compound 1)

In a 1000 ml single-neck reaction flask, 700 ml of acetic acid, 20 g (75 mmol) of 3,6-dibromo-1,2-benzenediamine, 16.4 g (78 mmol) of benzil and a stir bar were added, and then a condenser was installed. The reaction was carried out with stirring at 140° C. for 24 hours. After the completion of reaction, the solvent was removed by pressure reduction concentration and a crude product was obtained. The crude product was cleaned with water, dried, and then purified by column chromatography to obtain white, solid 5,8-dibromo-2,3-diphenylquinoxaline (yield: 64%). In a 250 ml two-neck flask, 60 ml of toluene, 1 g (0.86 mmol) of Pd(pph$_3$)$_4$ catalyst (tetrakis(triphenylphosphine)palladium), 5.5 g (40 mmol) of potassium carbonate (K$_2$CO$_3$), 40 ml (0.05M) of P$^t$Bu$_3$ (tri-tert-butylphosphine), 6.4 g (20 mmol) of 2-(9,9-dimethyl-9H-fluoren-2-yl)-4,4,5,5-tetramethyl-1,3,2-dioxaborolane, 4.4 g (10 mmol) of 5,8-dibromo-2,3-diphenylquinoxaline and a stir bar were added. The reaction was carried out with stirring at 120° C. for 3 days. After the completion of reaction, the solvent was removed by pressure reduction concentration, and an extraction was performed with methylene chloride and water. The resultant organic layer was further concentrated to obtain a solid product, which was purified by column chromatography to obtain a yellow solid product (yield: 30%).

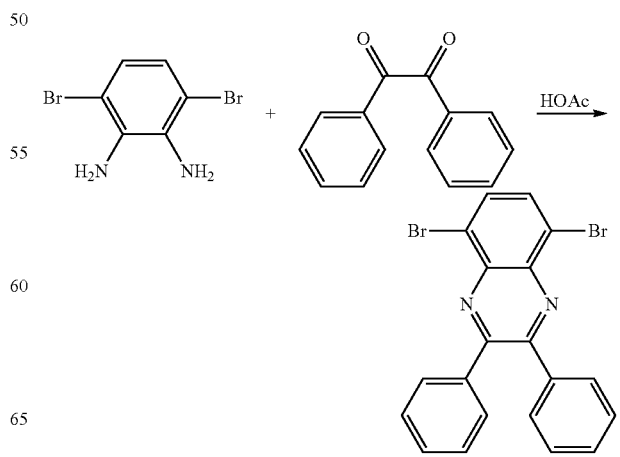

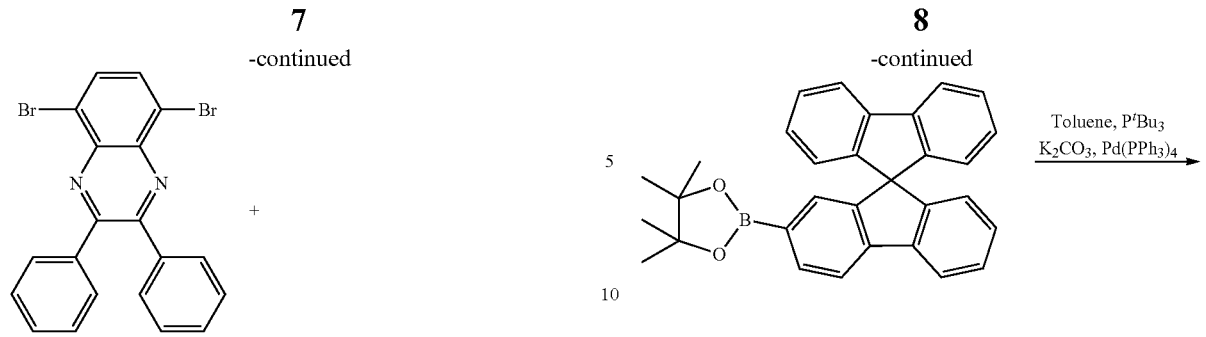

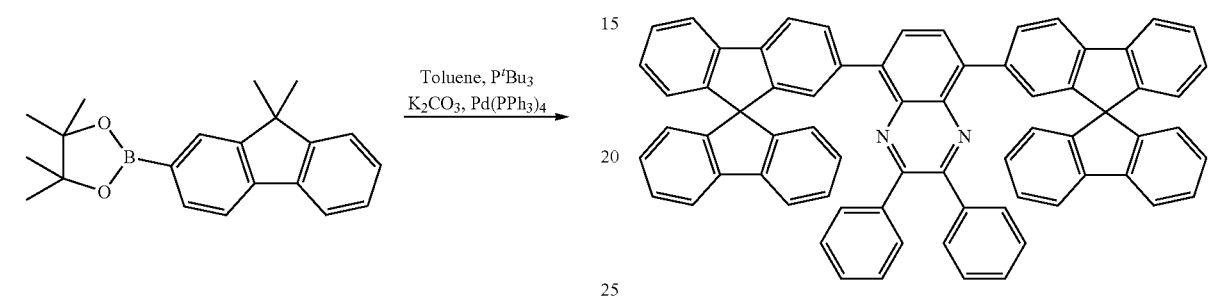

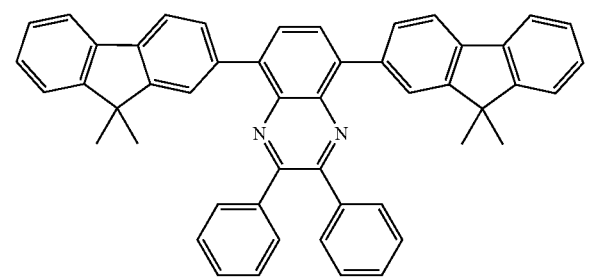

(The Synthesis of Compound 2)

In a 500 ml two-neck flask, 125 ml of toluene, 0.753 g (0.65 mmol) of Pd(pph₃)₄ catalyst, 3.3 g (23.8 mmol) of potassium carbonate, 5.5 g (12.4 mmol) of 2-pinacolato boronic ester-9,9'-spirobifluorenes, 2.49 g (5.65 mmol) of 5,8-dibromo-2,3-diphenylquinoxaline, 22.6 ml (0.05M) of P$^t$Bu₃ and a stir bar were added. The reaction was carried out with stirring under a nitrogen reflux at 110° C. for 48 hours. After the completion of reaction, the solvent was removed by pressure reduction concentration, and an extraction was performed with methylene chloride and water. The resultant organic layer was further concentrated to obtain a solid product, which was purified by column chromatography to obtain a yellow solid product of 2 g (yield: 39%).

(The Synthesis of Compound 3)

In a 250 ml three-neck flask, 125 ml of toluene, 0.5252 g (0.227 mmol) of Pd(pph₃)₄ catalyst, 9.54 ml (2 M) of potassium carbonate, 4.22 g (9.09 mmol) of 2-pinacolato boronic ester-9,9'-spirobifluorenes, 2 g (4.5441 mmol) of 2,3-bis(4-bromophenyl)quinoxaline, 9.08 ml (0.05 M) of P$^t$Bu₃ and a stir bar were added. The reaction was carried out with stirring at 113° C. for 24 hours. After the completion of reaction, the solvent was removed by pressure reduction concentration, and an extraction was performed with methylene chloride and water. The resultant organic layer was further concentrated to obtain a solid product, which was purified by column chromatography to obtain a yellow solid product of 2.5 g (yield: 60%).

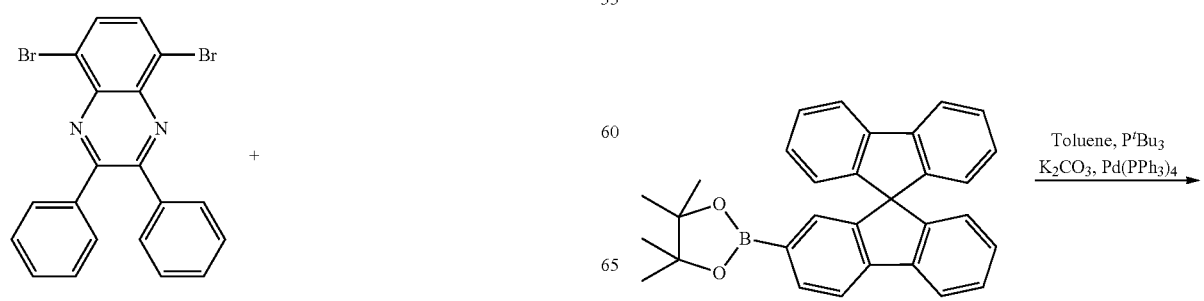

-continued

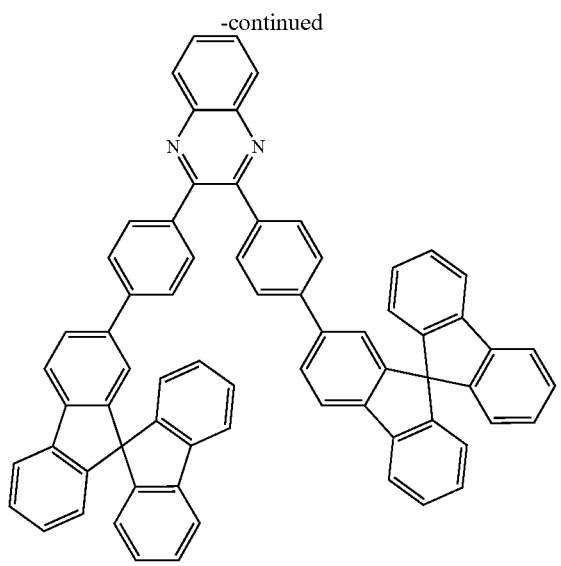

(The Synthesis of Compound 4)

In a 250 ml three-neck flask, 125 ml of toluene, 0.5252 g (0.227 mmol) of Pd(pph$_3$)$_4$ catalyst, 9.54 ml (2 M) of potassium carbonate, 2 g (4.5441 mmol) of 5,8-dibromo-2,3-diphenylquinoxaline, 3.041 g (9.09 mmol) of 9-(4,4,5,5-tetramethyl-1,3,2-dioxaborolan-2-yl)anthracene, 9.08 ml (0.05M) of P$^t$Bu$_3$ and a stir bar were added. The reaction was carried out with stirring under a nitrogen reflux for 4 days. After the completion of reaction, the solvent was removed by pressure reduction concentration, and an extraction was performed with methylene chloride and water. The resultant organic layer was further concentrated to obtain a solid product, which was purified by column chromatography to obtain a yellow-orange solid product of 0.7 g (yield: 24%).

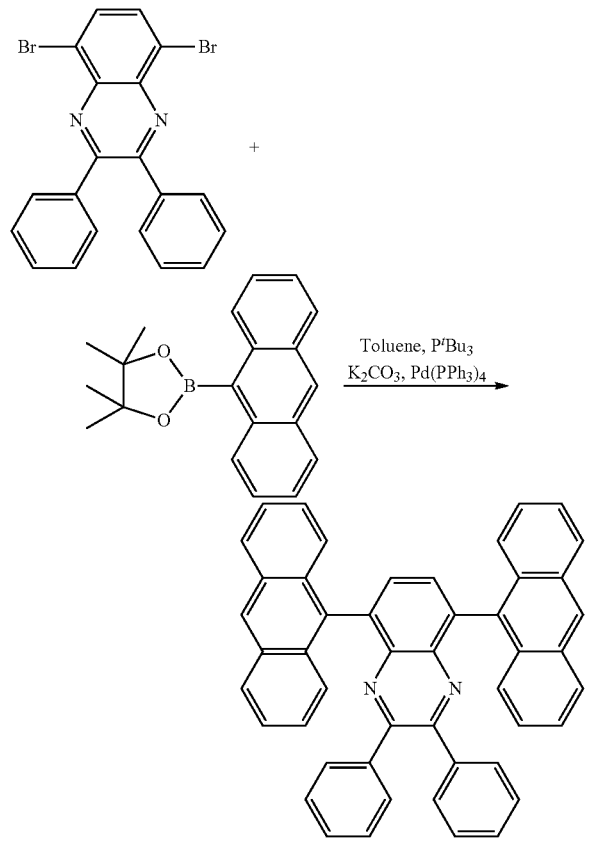

(The Synthesis of Compound 5)

In a 250 ml single-neck reaction flask, 100 ml of acetic acid, 1.38 g (1.65 mmol) of N1,N1,N4,N4-tetraphenylbenzene-1,2,3,4-tetraamine, 1.38 g (1.65 mmol) of 4,4'-di-(9,9'-spirobifluorenyl)benzil and a stir bar were added, and then a condenser was installed. The reaction was carried out with stirring at 130° C. for 24 hours. After the completion of reaction, the solvent was removed by pressure reduction concentration and an orange-red crude product was obtained. The crude product was purified by column chromatography to obtain a orange-red solid product (yield: 60%).

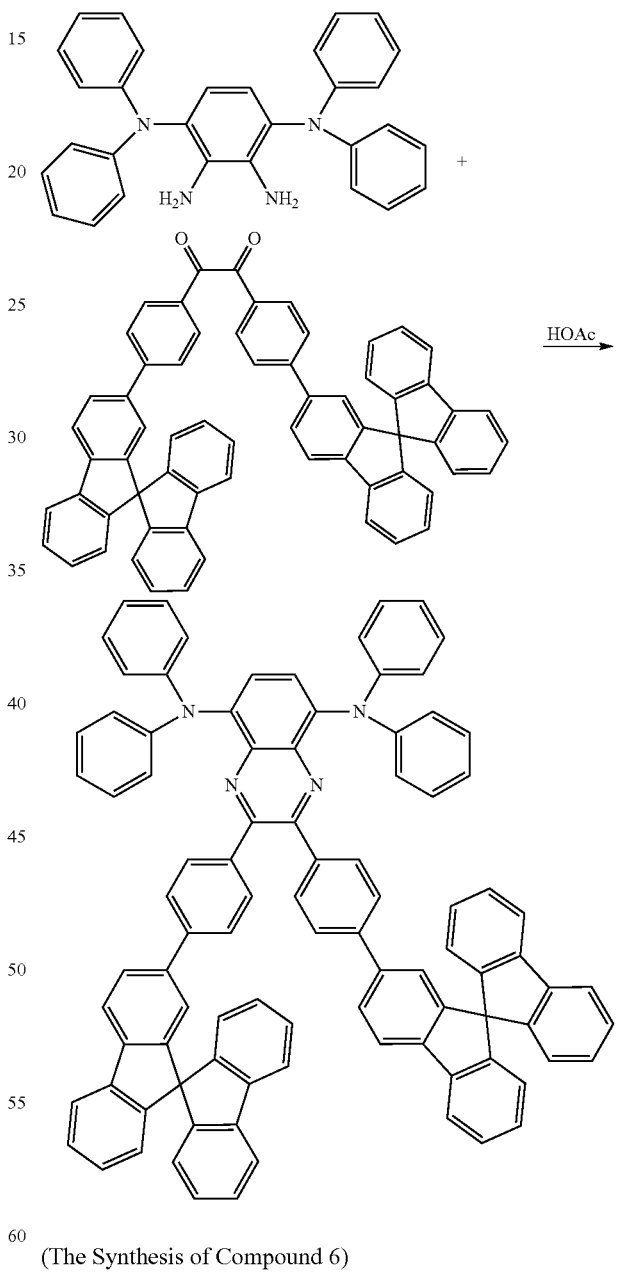

(The Synthesis of Compound 6)

In a 50 ml three-neck flask, 30 ml of toluene, 0.0116 g (0.0517 mmol) of Pd(OAc)$_2$ (Palladium diacetate), 0.1325 g (1.3785 mmol) of NaO$^t$Bu (Sodium tert-butoxide), 0.1283 g (0.7582 mmol) of diphenylamine, 4.13 ml (0.05 M) of P$^t$Bu$_3$, 0.2842 g (0.34463 mmol) of 2,3-bis(4-bromophenyl)-5,8-bis (9,9'-dimethyl-9H-fluoren-2-yl)quinoxaline and a stir bar were added. The reaction was carried out with stirring at 130° C. for 24 hours. After the completion of reaction, the solvent was removed by pressure reduction concentration, and an extraction was performed with methylene chloride and water. The resultant organic layer was further concentrated to obtain a solid product, which was purified by column chromatography to obtain a yellow solid product of 0.13 g (yield: 37%).

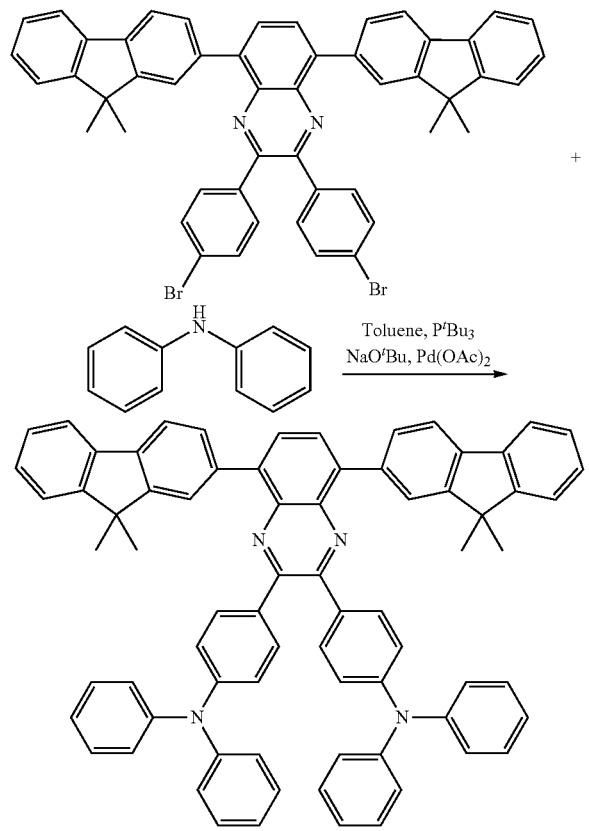

(Examples of Application)

The compounds of quinoxaline derivatives thus synthesized were applied to organic light-emitting diode devices. The composition and thickness of each layer of the devices are shown as below. A test on the properties of the devices was conducted and the test results are shown in Table 1.

Device 1
   anode ITO provided on glass substrate (thickness: 120 nm)
   hole transporting layer NPB (thickness: 40 nm)
   guest material Ir(ppy)$_3$ and host material CBP (4,4'-Bis(carbazol-9-yl)biphenyl) of emitting layer (thickness: 30 nm)
   hole blocking layer BCP (thickness: 5 nm)
   electron transporting layer Compound 1 (thickness: 25 nm)
   electron injection layer LiF (thickness: 0.3 nm)
   cathode Al (thickness: 120 nm)

Device 2
   anode ITO provided on glass substrate (thickness: 120 nm)
   hole transporting layer NPB (thickness: 40 nm)
   guest material Ir(ppy)$_3$ and host material CBP of emitting layer (thickness: 30 nm)
   hole blocking layer BCP (thickness: 5 nm)
   electron transporting layer Compound 3 (thickness: 25 nm)
   electron injection layer LiF (thickness: 0.3 nm)
   cathode Al (thickness: 120 nm)

Device 3
   anode ITO provided on glass substrate (thickness: 120 nm)
   hole transporting layer NPB (thickness: 40 nm)
   host material Compound 1 and guest material rubrene of emitting layer (thickness: 25 nm)
   electron transporting layer Alq3 (thickness: 30 nm)
   electron injection layer LiF (thickness: 0.3 nm)
   cathode Al (thickness: 120 nm)

Device 4
   anode ITO provided on glass substrate (thickness: 120 nm)
   hole transporting layer NPB (thickness: 40 nm)
   emitting layer and electron transporting layer Compound (thickness: 50 nm)
   electron injection layer LiF (thickness: 0.3 nm)
   cathode Al (thickness: 120 nm)

Device 5
   anode ITO provided on glass substrate (thickness: 120 nm)
   hole transporting layer Compound 5 (thickness: 40 nm)
   guest material Ir(ppy)$_3$ and host material CBP of emitting layer (thickness: 30 nm)
   hole blocking layer BCP (thickness: 5 nm)
   electron transporting layer Alq3 (thickness: 25 nm)
   electron injection layer LiF (thickness: 0.3 nm)
   cathode Al (thickness: 100 nm)

The structures of the aforementioned five devices can be simplified as below:

Device 1: ITO (120 nm)/NPB (40 nm)/Ir(ppy)$_3$:CBP (30 nm)/BCP (5 nm)/Compound 1 (25 nm)/LiF (0.3 nm)/Al (120 nm)

Device 2: ITO (120 nm)/NPB (40 nm)/Ir(ppy)$_3$:CBP (30 nm)/BCP (5 nm)/Compound 3 (25 nm)/LiF (0.3 nm)/Al (120 nm)

Device 3: ITO (120 nm)/NPB (40 nm)/rubrene:Compound 1 (25 nm)/Alq3 (30 nm)/LiF (0.3 nm)/Al (120 nm)

Device 4: ITO (120 nm)/NPB (40 nm)/Compound 1 (50 nm)/LiF (0.3 nm)/Al (120 nm)

Device 5: ITO (120 nm)/Compound 5 (40 nm)/Ir(ppy)$_3$:CBP (30 nm)/BCP (5 nm)/Alq3 (25 nm)/LiF (0.3 nm)/Al (100 nm)

TABLE 1

| Device | Operating Voltage (V) | Luminance (cd/m$^2$) | Chromaticity Coordinate (x, y) | Luminous Power Efficiency (lm/W) |
|---|---|---|---|---|
| Device 1 | 6.2 | 1000 | 0.31, 0.62 | 11.4 |
| Device 2 | 13.8 | 1000 | 0.31, 0.62 | 4.5 |
| Device 3 | 6.2 | 1000 | 0.49, 0.51 | 2.8 |
| Device 4 | 11.8 | 100 | 0.27, 0.54 | 0.1 |
| Device 5 | 12.8 | 1000 | 0.36, 0.57 | 0.7 |

Device 1 and Device 2 used Compound 1 and Compound 3 as the materials of the electron transporting layer, Device 3 used Compound 1 as the host material of the emitting layer, Device 4 used Compound 1 as the material of the electron transporting layer and emitting layer, and Device 5 used Compound 5 as the material of the hole transporting layer. From the result of the device test, it can be known that the quinoxaline derivatives of the present invention can be used as a hole transporting layer, a host or guest of an emitting layer or an electron transporting layer of an organic light-emitting diode device.

INDUSTRIAL APPLICABILITY

The novel quinoxaline derivatives of the present invention can be used as a hole transporting layer, a host or guest of an emitting layer or an electron transporting layer of an organic light-emitting diode device. Such materials can thus be used in light-emitting devices such as indicating device, electronic camera, luminescent beam, display, writing beam, reading beam, signal board, optical communication device, illumination device, etc.

While the present invention has been described above with reference to the preferred embodiments, it should not be considered as limited thereby. Various equivalent alterations and modifications made to its configuration and the embodiments by the skilled persons could be conceived of without departing from the scope of the present invention. All equivalent modifications based on the accompanying claims shall be included in the protective scope of the present invention.

What is claimed is:

1. A quinoxaline derivative having a structure represented by formula (1):

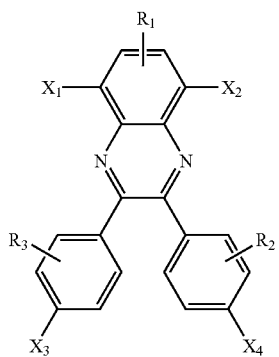

formula (1)

wherein $R_1$-$R_3$ are independently selected from the group consisting of hydrogen atom, amino group, $C_1$-$C_{20}$ fluorinated alkyl group, $C_3$-$C_{20}$ cycloalkyl group, $C_3$-$C_{20}$ fluorinated cycloalkyl group, $C_6$-$C_{20}$ aryl group, $C_6$-$C_{20}$ fluorinated aryl group, $C_4$-$C_{20}$ heterocyclic aryl group, $C_4$-$C_{20}$ fluorinated heterocyclic aryl group, $C_4$-$C_{20}$ alkylaryl group and $C_7$-$C_{20}$ fluorinated alkylaryl group and wherein $X_1$ and $X_2$ are each the structure represented by the formula (4) and wherein $X_3$ and $X_4$ are each structures represented by the formula (3):

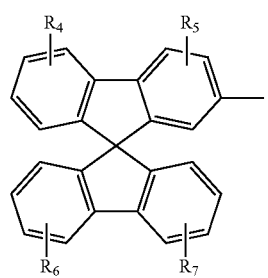

formula (3)

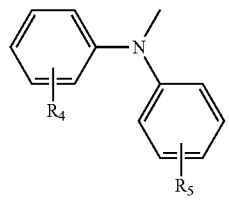

formula (4)

wherein $R_4$-$R_7$ are independently selected from the group consisting of hydrogen atom, amino group, $C_1$-$C_{20}$ fluorinated alkyl group, $C_3$-$C_{20}$ cycloalkyl group, $C_3$-$C_{20}$ fluorinated cycloalkyl group, $C_6$-$C_{20}$ aryl group, $C_6$-$C_{20}$ fluorinated aryl group, $C_4$-$C_{20}$ heterocyclic aryl group, $C_4$-$C_{20}$ fluorinated heterocyclic aryl group, $C_4$-$C_{20}$ alkylaryl group and $C_7$-$C_{20}$ fluorinated alkylaryl group.

2. A quinoxaline derivative according to claim 1, which is used as a host or guest material for an emitting layer.

3. A quinoxaline derivative according to claim 1, which is used as a material for an electron transporting layer.

4. A quinoxaline derivative according to claim 1, which is used as a material for a hole transporting layer.

5. An organic light-emitting diode device, characterized by having a quinoxaline derivative according to claim 1 between a pair of electrodes.

6. The organic light-emitting diode device according to claim 5, wherein the quinoxaline derivative is used as a host or guest material for an emitting layer, a material for a hole transporting layer or a material for an electron transporting layer of the organic light-emitting diode device.

7. A quinoxaline derivative according to claim 1, wherein said quinoxaline derivative has the following structure:

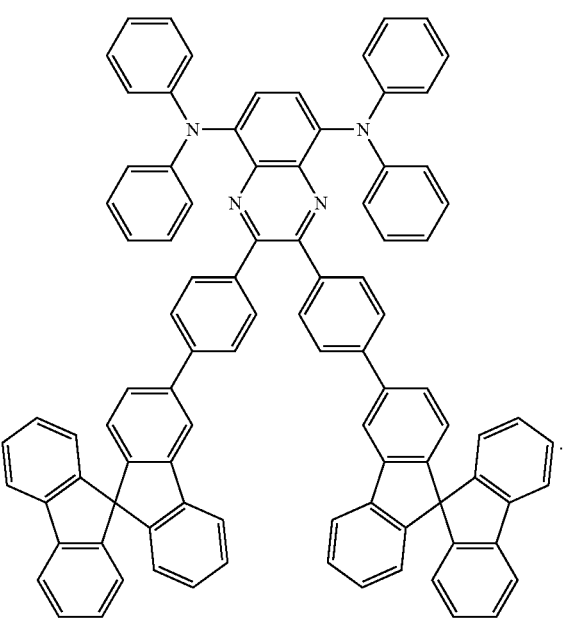 [SMILES: c1ccc(N(c2ccccc2)c2ccc(N(c3ccccc3)c3ccccc3)c3nc(-c4ccc(-c5ccc6c(c5)-c5ccccc5C65c6ccccc6-c6ccccc65)cc4)c(-c4ccc(-c5ccc6c(c5)-c5ccccc5C65c6ccccc6-c6ccccc65)cc4)nc23)cc1]

* * * * *